United States Patent
Hoshino

(10) Patent No.: US 11,154,490 B2
(45) Date of Patent: Oct. 26, 2021

(54) COMPOSITION FOR KERATIN FIBERS

(71) Applicant: L'OREAL, Paris (FR)

(72) Inventor: Akito Hoshino, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/461,228

(22) PCT Filed: Nov. 22, 2017

(86) PCT No.: PCT/JP2017/042699
§ 371 (c)(1),
(2) Date: May 15, 2019

(87) PCT Pub. No.: WO2018/097332
PCT Pub. Date: May 31, 2018

(65) Prior Publication Data
US 2019/0274949 A1 Sep. 12, 2019

(30) Foreign Application Priority Data
Nov. 28, 2016 (JP) .............................. JP2016-229837

(51) Int. Cl.
| | | |
|---|---|---|
| *A61K 9/00* | (2006.01) | |
| *A61K 8/92* | (2006.01) | |
| *A61K 8/06* | (2006.01) | |
| *A61K 8/19* | (2006.01) | |
| *A61K 8/36* | (2006.01) | |
| *A61K 8/41* | (2006.01) | |
| *A61K 8/891* | (2006.01) | |
| *A61Q 1/10* | (2006.01) | |

(52) U.S. Cl.
CPC .............. *A61K 8/922* (2013.01); *A61K 8/062* (2013.01); *A61K 8/19* (2013.01); *A61K 8/361* (2013.01); *A61K 8/41* (2013.01); *A61K 8/891* (2013.01); *A61K 8/925* (2013.01); *A61Q 1/10* (2013.01); *A61K 2800/43* (2013.01)

(58) Field of Classification Search
CPC .................................................... A61K 8/922
See application file for complete search history.

(56) References Cited

U.S. PATENT DOCUMENTS

| | | | |
|---|---|---|---|
| 6,045,783 A | 4/2000 | Macchio et al. | |
| 2010/0323042 A1 | 12/2010 | Collins et al. | |
| 2011/0236324 A1* | 9/2011 | Deo ...................... | A61Q 17/04 424/58 |
| 2014/0161898 A1 | 6/2014 | Collins et al. | |

FOREIGN PATENT DOCUMENTS

| | | |
|---|---|---|
| CN | 102961273 A | 3/2013 |
| DE | 202006001786 U1 | 5/2006 |
| FR | 2822068 A1 | 9/2002 |
| FR | 2886853 A1 | 12/2006 |
| JP | 2016-056110 A | 4/2016 |
| KR | 10-2013-040115 A | 12/2013 |
| KR | 10-2015-0080607 A | 7/2015 |
| KR | 10-2016-0133577 A | 11/2016 |

OTHER PUBLICATIONS

Machine translation of FR2822068A1, Dec. 2019 (Year: 2019).*
International Search Report for counterpart Application No. PCT/JP2017/042699, dated Mar. 20, 2018.
Mintel: "Waterproof Mascara," Avon, XP002778873, Database Accession No. 3360593, Jul. 2015.
Mintel: "Long Lash Mascara," Boots, XP002778874, Database Accession No. 4058833, Jun. 2016.
Mintel: "Long Lash Mascara," Boots, XP002778875, Database Accession No. 4415041, Nov. 2016.
Mintel: "Brightening Moisture Lotion," Origins Natural Resources, XP002778876, Database Accession No. 432364, Mar. 2006.
Mintel: "Refreshing Eye Cream" Origins Natural Resources, XP002778877, Database Accession No. 1195002, Oct. 2009.
Mintel: "Body Care," Laboratoires Sante Beaute, XP002778879, Database Accession No. 85373, Jan. 2001.
Mintel: "The Rich Cream," Gueriain, XP002778878, Database Accession No. 2166407, Oct. 2013.
Translated Korean Office Action for counterpart Application No. 10-2019-7014524, dated Oct. 13, 2020.
Mintel: "Volume Mascara," Aldi, ID 1852311, Aug. 2012.
Mintel: "Volume Mascara," Netto, ID 4046623, Jun. 2016.
Mintel: "Volume Mascara," Etude, ID 1790072, May 2012.
Mintel: "Fillercara Mascara," Innisfree, ID 4002129, May 2016.
Mintel: "Daily Proof Waterproof Mascara," The Face Shop, ID 2801881, Dec. 2014.
Mintel, "Mascara Mega," LG Household & Health Care, ID 2584351, Aug. 2014.
Mintel: "Body Performance Firming Body Creme," Estee Lauder, ID 264444, Apr. 2004.
Japanese Office Action for counterpart Application No. 2016-229837, dated Nov. 2, 2020, with translation.
Korean Decision to Grant for counterpart Application No. 10-2019-7014524, dated Apr. 27, 2021, with translation.
First Office Action for counterpart Chinese Application No. 201780072525.8, dated Aug. 3, 2021, with translation.

* cited by examiner

*Primary Examiner* — Paul W Dickinson
(74) *Attorney, Agent, or Firm* — The Marbury Law Group, PLLC

(57) ABSTRACT

The present invention relates to a composition comprising: (a) at least one botanical butter; (b) at least one alkaline agent comprising at least one primary amino group and at least three hydroxyl groups; (c) at least one wax; and (d) water. The composition according to the present invention does not produce NDELA, because it does not need to use TEA, but it can provide keratin fibers such as eyelashes with enhanced or improved cosmetic effects or properties, such as excellent volumizing effects (e.g., the thickness of keratin fibers is increased) and even application effects (e.g., the composition can be applied evenly onto keratin fibers to clean appearance of the keratin fibers).

13 Claims, No Drawings

COMPOSITION FOR KERATIN FIBERS

CROSS REFERENCE TO RELATED APPLICATION

This is a national stage application of PCT/JP2017/042699, filed internationally on Nov. 22, 2017, which claims priority to Japanese Application No. 2016-229837, filed on Nov. 28, 2016, both of which are incorporated by reference herein in their entireties.

TECHNICAL FIELD

The present invention relates to a composition for keratin fibers, preferably a cosmetic composition, more preferably a makeup cosmetic composition, and in particular a mascara, as well as a process and use which relate to the composition.

BACKGROUND ART

Mascaras are commonly prepared as two types of wax-based formulations:
aqueous mascaras, known as cream mascaras, in the form of an emulsion of waxes in water; and
anhydrous mascaras or mascaras with a low water content, known as waterproof mascaras, in the form of a dispersion of waxes in volatile organic solvents.

For aqueous mascaras, triethanolamine (TEA) is commonly used as an alkaline agent which can react with a fatty acid such as stearic acid to form a fatty acid-TEA soap. The stearic acid-TEA soap can provide keratin fibers such as eyelashes with volumizing effects. However, TEA is sometimes able to produce N-nitrosodiethanolamine (NDELA). NDELA is well known as a substance which may cause cancer, and therefore, NDELA should not be in cosmetics including mascara.

DISCLOSURE OF INVENTION

Other alkaline agents such as amnomethyl propanol (AMP), aminomethyl propandiol (AMPD) and tromethamine (TRIS) do not produce NDELA. Therefore, it may be useful to use these alkaline agents instead of TEA. However, the level of the cosmetic effects provided by TEA should not be compromised or deteriorated.

An objective of the present invention is to provide a composition suitable for keratin fibers, which does not produce NDELA and can provide the keratin fibers with enhanced or improved cosmetic effects, such as excellent volumizing effects and even application effects.

The above objective can be achieved by a composition for keratin fibers, comprising:
(a) at least one botanical butter;
(b) at least one alkaline agent comprising at least one primary amino group and at least three hydroxyl groups;
(c) at least one wax; and
(d) water.

It is preferable that the (a) botanical butter have a melting point of less than 60° C., preferably from 40 to 58° C., and more preferably from 45 to 55° C.

It is preferable that the (a) botanical butter be jojoba butter.

The amount of the (a) botanical butter(s) in the composition according to the present invention may be 0.01% to 20% by weight, preferably 0.1% to 10% by weight, and more preferably 1% to 5% by weight, relative to the total weight of the composition.

It is preferable that the (b) alkaline agent comprise one primary amino group and three hydroxyl groups. It is more preferable that the (b) alkaline agent be represented by the formula: $H_2N-C\{(CH_2)_nOH\}_3$ wherein n denotes an integer from 0 to 5, preferably from 1 to 5, and more preferably from 1 to 3. It is even more preferable that the (b) alkaline agent be tromethamine.

The amount of the (b) alkaline agent(s) in the composition according to the present invention may be 0.01% to 20% by weight, preferably 0.1% to 15% by weight, and more preferably 0.5% to 10% by weight, relative to the total weight of the composition.

It is preferable that the (c) wax(es) have a melting point of greater than or equal to 60° C.

The amount of the (c) wax(es) in the composition according to the present invention may be 1% to 40% by weight, preferably 5% to 35% by weight, and more preferably 10% to 25% by weight, relative to the total weight of the composition.

The amount of the (d) water in the composition according to the present invention may be 25% to 75% by weight, preferably 35% to 65% by weight, and more preferably 45% to 55% by weight, relative to the total weight of the composition.

The composition according to the present invention may further comprise (e) at least one fatty acid.

The amount of the (e) fatty acid(s) in the composition according to the present invention may be 0.01% to 20% by weight, preferably 0.1% to 10% by weight, and more preferably 1% to 5% by weight, relative to the total weight of the composition It is preferable that the (b) alkaline agent(s) form(s) a soap or soaps with the (e) fatty acid(s).

The composition according to the present invention may further comprise particles selected from fillers and pigments, and preferably further comprises at least one filler and at least one pigment.

The pigment may be selected from metallic oxides, preferably from iron oxides. The filler may be selected from silicone elastomers, in particular from those having the INCI name of Dimethicone/Vinyl Dimethicone Crosspolymer.

The amount of the particle(s) in the composition may be 2% by weight or more, preferably from 3 to 15% by weight, relative to the total weight of the composition.

The composition according to the present invention may further comprise at least one non-ionic surfactant, preferably selected from non-ionic surfactant(s) having HLB value of greater than or equal to 8.

The composition according to the present invention may be a cosmetic composition, preferably a makeup composition, and more preferably a mascara composition.

Another aspect of the present invention relates to a cosmetic process for making up keratin fibers, comprising the step of applying onto the keratin fibers the composition according to the present invention.

BEST MODE FOR CARRYING OUT THE INVENTION

After diligent research, the inventors have discovered that it is possible to provide a composition suitable for keratin fibers, which does not produce NDELA and can provide the keratin fibers with enhanced or improved cosmetic effects, such as excellent volumizing effects and even application effects.

Thus, the composition according to the present invention is a composition, comprising:
(a) at least one botanical butter;
(b) at least one alkaline agent comprising at least one primary amino group and at least three hydroxyl groups;
(c) at least one wax; and
(d) water.

The composition according to the present invention does not produce NDELA, because it does not need to use TEA, but it can provide keratin fibers such as eyelashes with enhanced or improved cosmetic effects or properties, such as excellent volumizing effects (e.g., the thickness of keratin fibers is increased) and even application effects (e.g., the composition can be applied evenly onto keratin fibers for a clean appearance of the keratin fibers).

Hereafter, the composition, as well as the process, according to the present invention will be described in a detailed manner.

[Composition]

(Botanical Butter)

The composition according to the present invention comprises (a) at least one botanical butter. If two or more botanical butters are used, they may be the same or different.

As used herein, a "botanical butter" is a fat and/or oil extract of a plant fruit and/or seed characterized by having emollient properties and a melting point near human body temperature.

It is preferable that the (a) botanical butter have a melting point of higher than or equal to 35° C., more preferably higher than or equal to 40° C., and even more preferably higher than or equal to 45° C. It is preferable that the (a) botanical butter have a melting point of less than 60° C., more preferably up to 58° C., and even more preferably up to 55° C.

It is preferable that the (a) botanical butter have a melting point of from 35 to 60° C., more preferably from 40 to 58° C., and even more preferably from 45 to 55° C.

The (a) botanical butter may include both pure extracts from a plant fruit or seed and/or extract from a plant fruit or seed combined with additional lipid material to achieve the melting point characteristic and/or lubricity.

The (a) botanical butter may be derived from a botanical source.

Exemplary botanical butters include, but are not limited to, mango seed butter, raspberry butter, avocado butter, shea butter, olive butter, kuku butter, monoi butter, peach butter, pistachio butter, coconut butter, cocoa butter, pomegranate butter, rose hip butter, sunflower butter, wheat germ butter, apricot butter, babassu butter, cupuacu butter, kokum butter, hazelnut butter, jojoba butter, sesame butter, soy butter, almond butter, meadowfoam seed butter, black current seed butter and cranberry butter.

It is preferable that the (a) botanical butter be jojoba butter (*Simmondsia Chinensis* butter). The jojoba butter can be obtained by the isomerization of *Simmondsia Chinensis* (Jojoba) seed oil. It is preferable to use jojoba butter which has a melting point preferably from 45 to 55° C. An example of the jojoba butter that may be mentioned is the product sold under the name ISO JOJOBA 50 by the company DESERT WHALE which has a melting point of 50° C.

The amount of the (a) botanical butter(s) in the composition according to the present invention may be 0.01% by weight or more, preferably 0.1% by weight or more, and more preferably 1% by weight or more, relative to the total weight of the composition. It may be even more preferable that the amount of the (a) botanical butter(s) in the composition according to the present invention be 1.5% by weight or more, relative to the total weight of the composition.

On the other hand, the amount of the (a) botanical butter(s) in the composition according to the present invention may be 20% by weight or less, preferably 10% by weight or less, and more preferably 5% by weight or less, relative to the total weight of the composition. It may be even more preferable that the amount of the (a) botanical butter(s) in the composition according to the present invention be 3% by weight or less, relative to the total weight of the composition.

Accordingly, the amount of the (a) botanical butter(s) in the composition may range from 0.01% to 20% by weight, preferably from 0.1% to 10% by weight, and more preferably from 1% to 5% by weight, relative to the total weight of the composition. It may be even more preferable that the amount of the (a) botanical butter(s) in the composition according to the present invention be from 1.5% to 3% by weight, relative to the total weight of the composition.

(Alkaline Agent)

The composition according to the present invention comprises (b) at least one alkaline agent comprising at least one primary amino group and at least three hydroxyl groups. If two or more such alkaline agents are used, they may be the same or different.

It is possible for the (b) alkaline agent to comprise a combination of, for example, one primary amino group and three hydroxyl groups, two primary amino groups and three hydroxyl amino groups, and three primary amino groups and three hydroxyl groups.

It is preferable that the (b) alkaline agent comprise one primary amino group and three hydroxyl groups.

The (b) alkaline agent may or may not comprise at least one secondary or tertiary amino group. However, it is preferable that the (b) alkaline agent comprises no secondary or tertiary amino group.

It is more preferable that the (b) alkaline agent be represented by the formula: $H_2N-C\{(CH_2)_nOH\}_3$ wherein n denotes an integer from 0 to 5, preferably from 1 to 5, and more preferably from 1 to 3.

It is even more preferable that the (b) alkaline agent be tromethamine.

The amount of the (b) alkaline agent(s) in the composition according to the present invention may be 0.01% by weight or more, preferably 0.1% by weight or more, and more preferably 0.5% by weight or more, relative to the total weight of the composition. It may be even more preferable that the amount of the (b) alkaline agent(s) in the composition according to the present invention be 1% by weight or more, relative to the total weight of the composition.

On the other hand, the amount of the (b) alkaline agent(s) in the composition according to the present invention may be 20% by weight or less, preferably 15% by weight or less, and more preferably 10% by weight or less, relative to the total weight of the composition. It may be even more preferable that the amount of the (b) alkaline agent(s) in the composition according to the present invention be 5% by weight or less, relative to the total weight of the composition.

Accordingly, the amount of the (b) alkaline agent(s) in the composition may range from 0.01% to 20% by weight, preferably from 0.1% to 15% by weight, and more preferably from 0.5% to 10% by weight, relative to the total weight of the composition. It may be even more preferable that the amount of the (b) alkaline agent(s) in the composition according to the present invention be from 1% to 5% by weight, relative to the total weight of the composition.

(Fatty Acid)

The composition according to the present invention may further comprise (e) at least one fatty acid. If two or more (e) fatty acids are used, they may be the same or different.

The term "fatty acid" here means a carboxylic acid with a long aliphatic carbon chain. It is preferable that the fatty acid be selected from any saturated or unsaturated, linear or branched fatty acids.

It is preferable that the (e) fatty acid be selected from $C_{16}$-$C_{24}$ fatty acid, more preferably $C_{16}$-$C_{22}$ fatty acid, and even more preferably $C_{16}$-$C_{20}$ fatty acid.

Mention may be made among these of palmitic acid, margaric acid, stearic acid, nonadecylic acid, arachidic acid, heneicosylic acid, behenic acid, tricosylic acid, lignoceric acid, and mixtures thereof.

The (b) alkaline agent(s) can form a soap or soaps with the (e) fatty acid(s). The soap may function as an anionic surfactant.

As the (b) alkaline agent to form a soap with the (e) fatty acid(s), tromethamine may be preferable. In particular, it is preferable that tromethamine form a soap with stearic acid.

The amount of the (e) fatty acid(s) in the composition according to the present invention may be 0.01% by weight or more, preferably 0.1% by weight or more, and more preferably 1% by weight or more, relative to the total weight of the composition. It may be even more preferable that the amount of the (e) fatty acid(s) in the composition according to the present invention be 2% by weight or more, relative to the total weight of the composition.

On the other hand, the amount of the (e) fatty acid(s) in the composition according to the present invention may be 20% by weight or less, preferably 10% by weight or less, and more preferably 5% by weight or less, relative to the total weight of the composition. It may be even more preferable that the amount of the (e) fatty acid(s) in the composition according to the present invention be 3% by weight or less, relative to the total weight of the composition.

Accordingly, the amount of the (e) fatty acid(s) in the composition may range from 0.01% to 20% by weight, preferably from 0.1% to 10% by weight, and more preferably from 1% to 5% by weight, relative to the total weight of the composition. It may be even more preferable that the amount of the (e) fatty acid(s) in the composition according to the present invention be from 2% to 3% by weight, relative to the total weight of the composition.

(Wax)

The composition according to the present invention comprises (c) at least one wax. If two or more waxes are used, they may be the same or different.

The term "wax" means a lipophilic compound, which is solid at room temperature (25° C.), with a reversible solid/liquid change of state, having a melting point of greater than or equal to 30° C., which may be up to 120° C. In particular, the waxes have a melting point of greater than or equal to 30° C. and better still greater than or equal to 45° C.

For the purposes of the invention, the melting point is measured, for example in accordance with ASTM D127.

The wax used in the composition according to the invention advantageously has a melting point of greater than or equal to 60° C., preferably greater than or equal to 65° C., and more preferably greater than or equal to 75° C. The wax used in the composition according to the invention advantageously has a melting point of up to 90° C., preferably up to 85° C.

The wax advantageously has a hardness at 20° C. of greater than 5 MPa, and especially ranging from 5 to 15 MPa.

The hardness of the wax is determined by measuring the compressive force, measured at 20° C. using the texturometer sold under the name TA-XT2 by the company Rheo, equipped with a stainless-steel cylinder 2 mm in diameter, travelling at a measuring speed of 0.1 mm/second, and penetrating the wax to a penetration depth of 0.3 mm.

The measuring protocol of the hardness is as follows:

The wax is melted at a temperature equal to the melting point of the wax+10° C. The molten wax is poured into a container 25 mm in diameter and 20 mm deep. The wax is recrystallized at room temperature (25° C.) for 24 hours such that the surface of the wax is flat and smooth, and the wax is then stored for at least 1 hour at 20° C. before measuring the hardness or the tack.

The texturometer spindle is displaced at a speed of 0.1 mm/s, and then penetrates the wax to a penetration depth of 0.3 mm. When the spindle has penetrated the wax to a depth of 0.3 mm, the spindle is held still for 1 second (corresponding to the relaxation time) and is then withdrawn at a speed of 0.5 mm/s.

The hardness value is the maximum compression force measured divided by the area of the texturometer cylinder in contact with the wax.

Examples of the wax used in the present invention include a natural wax and a synthetic wax. Examples of the natural wax include a petroleum wax, a plant wax, and an animal wax. Examples of the petroleum wax include a paraffin wax, a microcrystalline wax, and a petrolatum. Examples of the plant wax include rice wax, carnauba wax, candelilla wax, ouricury wax, Japan wax, cocoa butter, cork fibre wax and sugarcane wax. Examples of the animal wax include lanolin wax, lanolin derivatives and beeswax. Examples of the synthetic wax include a synthetic hydrocarbon wax and a modified wax.

It is preferable that the composition of the present invention comprise carnauba wax. It is also preferable that the composition of the present invention comprise bees wax. It is more preferable that the composition of the present invention comprise carnauba wax and bees wax. Carnauba wax has a melting point of from 80 to 83° C. and bees wax has a melting point of 65° C.

Examples of the synthetic hydrocarbon wax include polyethylene wax, polypropylene wax, and Fischer-Tropsch wax. Examples of the modified wax include a paraffin wax derivative, a montan wax derivative, and a microcrystalline wax derivative. It is preferable that the (b) wax be selected from a synthetic hydrocarbon wax such as a polyethylene wax, a polypropylene wax, and a Fischer-Tropsch wax.

Examples of the polyethylene wax include an ethylene homopolymer and an ethylene-alpha-olefin copolymer. Alternatively, the wax may be obtained by thermal decomposition, of the copolymer. Examples of the alpha-olefin include an alpha-olefin having 3 to 12 carbon atoms such as propylene, 1-butene, 1-pentene, 1-hexene, 4-methyl-1-pentene, and 1-octene.

Examples of the polypropylene wax include a propylene homopolymer, an ethylene-propylene copolymer (which is a random or block copolymer), propylene-alpha-olefin (except for ethylene or propylene) copolymer. Alternatively, the wax may be obtained by thermal decomposition of the copolymer. Examples of the alpha-olefin include 1-butene, 1-pentene, 1-hexene, 1-heptene, 1-octene, 4-methyl-1-pentene, 1-decene, 1-dodecene, 1-tetradecene, 1-hexadecene, and 1-octadecene.

The polyethylene wax and the polypropylene wax can be obtained by a known method using a polymerization catalyst such as a Ziegler catalyst, a Ziegler-Natta catalyst, and a metallocene catalyst. In particular, the polyethylene wax and the polypropylene wax obtained by using a metallocene catalyst as a polymerization catalyst are preferable, having a narrow molecular weight distribution and stable quality, in comparison with the polyethylene wax and the polypropylene wax obtained by using a Ziegler catalyst or a Ziegler-Natta catalyst as a polymerization catalyst.

The Fischer-Tropsch wax is a synthetic hydrocarbon wax mainly comprising linear hydrocarbons, which is obtained by reacting water gas containing carbon monoxide and hydrogen as main components under normal pressure at 170 to 250° C. using a catalyst such as cobalt, nickel, or iron. The Fischer-Tropsch wax is characterized in comprising hydrocarbons containing odd and even numbers of carbon atoms, namely comprising both hydrocarbons containing odd numbers of carbon atoms and hydrocarbons containing even numbers of carbon atoms. Most preferably, the wax according to the present invention is Fisher-Tropsch wax.

The amount of the (c) wax(es) having a melting point of greater than or equal to 60° C., in the composition according to the present invention may be 1% by weight or more, preferably 5% by weight or more, and more preferably 10% by weight or more, relative to the total weight of the composition. It may be even more preferable that the amount of the (c) wax(es) having a melting point of greater than or equal to 60° C., in the composition according to the present invention be 10% by weight or more, relative to the total weight of the composition.

On the other hand, the amount of the (c) wax(es) having a melting point of greater than or equal to 60° C., in the composition according to the present invention may be 40% by weight or less, preferably 35% by weight or less, and more preferably 25% by weight or less, relative to the total weight of the composition. It may be even more preferable that the amount of the (c) wax(es) having a melting point of greater than or equal to 60° C., in the composition according to the present invention be 17% by weight or less, relative to the total weight of the composition.

Accordingly, the amount of the (c) wax(es) having a melting point of greater than or equal to 60° C., in the composition may range from 1% to 40% by weight, preferably from 5% to 35% by weight, and more preferably from 10% to 25% by weight, relative to the total weight of the composition. It may be even more preferable that the amount of the (c) wax(es) having a melting point of greater than or equal to 60° C., in the composition according to the present invention be from 10% to 17% by weight, relative to the total weight of the composition.

It is preferable that the amount of the (c) wax(es) having a melting point of greater than or equal to 75° C. such as carnauba wax in the composition according to the present invention be 0.1% by weight or more, preferably 1% by weight or more, and more preferably 5% by weight or more, relative to the total weight of the composition.

On the other hand, the amount of the (c) wax(es) having a melting point of greater than or equal to 75° C. such as carnauba wax in the composition according to the present invention may be 15% by weight or less, preferably 10% by weight or less, and more preferably 9% by weight or less, relative to the total weight of the composition.

Accordingly, the amount of the (c) wax(es) having a melting point of greater than or equal to 75° C. such as carnauba wax in the composition may range from 0.1% to 15% by weight, preferably from 1% to 10% by weight, and more preferably from 5% to 9% by weight, relative to the total weight of the composition.

It is preferable that the amount of the (c) wax(es) having a melting point of from 60 to 70° C. such as bees wax in the composition according to the present invention be 0.1% by weight or more, preferably 5% by weight or more, and more preferably 7% by weight or more, relative to the total weight of the composition.

On the other hand, the amount of the (c) wax(es) having a melting point of from 60 to 70° C. such as bees wax in the composition according to the present invention may be 18% by weight or less, preferably 15% by weight or less, and more preferably 10% by weight or less, relative to the total weight of the composition.

Accordingly, the amount of the (c) wax(es) having a melting point of from 60 to 70° C. such as bees wax in the composition may range from 0.1% to 18% by weight, preferably from 5% to 15% by weight, and more preferably from 7% to 10% by weight, relative to the total weight of the composition.

[Water]

The composition according to the present invention may comprise (d) water.

It is preferable that the composition according to the present invention be in the form of a wax-in-water emulsion. The term "wax-in-water emulsion" means any macroscopically homogeneous composition comprising a continuous water or aqueous phase and wax phases (at least one wax is included) in the form of droplets dispersed in the said water or aqueous phase.

It is preferable that, if the composition according to the present invention comprises (f) at least one oil explained below, the composition according to the present invention be in the form of an O/W emulsion.

The term "O/W emulsion" or "oil-in-water emulsion" means any macroscopically homogeneous composition comprising a continuous water or aqueous phase and oily phases (oil and wax are included) in the form of droplets dispersed in the said water or aqueous phase.

The amount of the (d) water in the composition according to the present invention may be 25% by weight or more, preferably 35% by weight or more, and more preferably 45% by weight or more, relative to the total weight of the composition. The amount of the (d) water in the composition according to the present invention may be 75% by weight or less, preferably 65% by weight or less, more preferably 55% by weight or less, relative to the total weight of the composition.

The amount of the (d) water in the composition according to the present invention may be from 25 to 75% by weight, preferably from 35 to 65% by weight, more preferably from 45 to 55% by weight, relative to the total weight of the composition.

(Oil)

The composition according to the present invention may further comprise (f) at least one oil. If two or more (f) oils are used, they may be the same or different.

Here, "oil" means a fatty compound or substance which is in the form of a liquid or a paste (non-solid) at room temperature (25° C.) under atmospheric pressure (760 mmHg). As the oils, those generally used in cosmetics can be used alone or in combination thereof. These oils may be volatile or non-volatile.

The (f) oil may be a non-polar oil such as a hydrocarbon oil, a silicone oil, or the like; a polar oil such as a plant or animal oil and an ester oil or an ether oil; or a mixture thereof.

The (f) oil may be selected from the group consisting of oils of plant or animal origin, synthetic oils, silicone oils, hydrocarbon oils, and fatty alcohols.

As examples of plant oils, mention may be made of, for example, linseed oil, camellia oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of animal oils, mention may be made of, for example, squalene and squalane.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate, and isostearyl neopentanoate.

Esters of $C_4$-$C_{22}$ dicarboxylic or tricarboxylic acids and of $C_1$-$C_{22}$ alcohols, and esters of monocarboxylic, dicarboxylic, or tricarboxylic acids and of non-sugar $C_4$-$C_{26}$ dihydroxy, trihydroxy, tetrahydroxy, or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides, or polysaccharides.

Examples of suitable sugars that may be mentioned include sucrose (or saccharose), glucose, galactose, ribose, fucose, maltose, fructose, mannose, arabinose, xylose, and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters, and polyesters, and mixtures thereof.

These esters may be, for example, oleates, laurates, palmitates, myristates, behenates, cocoates, stearates, linoleates, linolenates, caprates, and arachidonates, or mixtures thereof such as, especially, oleopalmitate, oleostearate, and palmitostearate mixed esters, as well as pentaerythrityl tetraethyl hexanoate.

More particularly, use is made of monoesters and diesters and especially sucrose, glucose, or methylglucose monooleates or dioleates, stearates, behenates, oleopalmitates, linoleates, linolenates, and oleostearates.

An example that may be mentioned is the product sold under the name Glucate® DO by the company Amerchol, which is a methylglucose dioleate.

As examples of preferable ester oils, mention may be made of, for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of, for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate), and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, the silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's *Chemistry and Technology of Silicones* (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylal kylsiloxane, such as Silicone Volatile® FZ 3109 sold by the company Union Carbide, of formula:

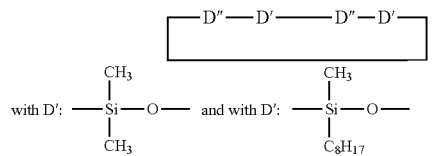

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2', 2',3,3'-hexatrimethylsilyloxy)neopentane; and (ii) linear volatile polydialkylsiloxanes containing 2 to 9 silicon atoms and having a viscosity of less than or equal to $5\times10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s; and the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups, mention may be made of polydiarylsiloxanes, especially polydiphenylsiloxanes and polyalkylarylsiloxanes such as phenyl silicone oil.

The phenyl silicone oil may be chosen from the phenyl silicones of the following formula:

in which $R_1$ to $R_{10}$, independently of each other, are saturated or unsaturated, linear, cyclic or branched $C_1$-$C_{30}$ hydrocarbon-based radicals, preferably $C_1$-$C_{12}$ hydrocarbon-based radicals, and more preferably $C_1$-$C_6$ hydrocarbon-based radicals, in particular methyl, ethyl, propyl, or butyl radicals, and m, n, p, and q are, independently of each other, integers of 0 to 900 inclusive, preferably 0 to 500 inclusive, and more preferably 0 to 100 inclusive, with the proviso that the sum n+m+q is other than 0.

Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250, and SF 1265.

As the phenyl silicone oil, phenyl trimethicone ($R_1$ to $R_{10}$ are methyl; p, q, and n=0; m=1 in the above formula) is preferable.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, $C_6$-$C_{16}$ lower alkanes. Examples that may be mentioned include hexane, undecane, dodecane, tridecane, and isoparaffins, for instance isohexadecane, isododecane, and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within

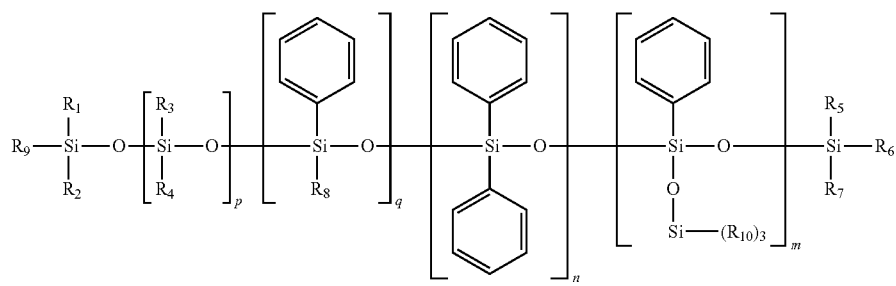

the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that the fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of lauryl alcohol, cetyl alcohol, stearyl alcohol, isostearyl alcohol, behenyl alcohol, undecylenyl alcohol, myristyl alcohol, octyldodecanol, hexyldecanol, and mixtures thereof. In one embodiment, cetyl alcohol, stearyl alcohol, octyldodecanol, hexyldecanol, or a mixture thereof (e.g., cetearyl alcohol) as well as behenyl alcohol, can be used as a saturated fatty alcohol.

According to at least one embodiment, the fatty alcohol used in the composition according to the present invention is preferably chosen from cetyl alcohol, octyldodecanol, hexyldecanol, and mixtures thereof.

The amount of the (f) oil(s) in the composition according to the present invention may be 0.01% by weight or more, preferably 0.1% by weight or more, and more preferably 1% by weight or more, relative to the total weight of the composition. It may be even more preferable that the amount of the (f) oil(s) in the composition according to the present invention be 5% by weight or more, relative to the total weight of the composition.

On the other hand, the amount of the (f) oil(s) in the composition according to the present invention may be 30% by weight or less, preferably 25% by weight or less, and more preferably 20% by weight or less, relative to the total weight of the composition. It may be even more preferable that the amount of the (f) oil(s) in the composition according to the present invention be 10% by weight or less, relative to the total weight of the composition.

Accordingly, the amount of the (f) oil(s) in the composition may range from 0.01% to 30% by weight, preferably from 0.1% to 25% by weight, and more preferably from 1% to 20% by weight, relative to the total weight of the composition. It may be even more preferable that the amount of the (f) oil(s) in the composition according to the present invention be from 5% to 10% by weight, relative to the total weight of the composition.

(Film-Forming Polymer)

The composition according to the present invention may further comprise (g) at least one film-forming polymer. If two or more (g) film-forming polymers are used, they may be the same or different.

For the purposes of the present invention, the term "polymer" means a compound corresponding to the repetition of one or more units (these units being derived from compounds known as monomers). This or these units(s) are repeated at least twice and preferably at least three times.

The term "film-forming polymer" means a polymer that is capable of forming, by itself or in the presence of an auxiliary film-forming agent, a macroscopically continuous film that adheres to a support, especially to keratin materials, preferably a cohesive film, and better still a film whose cohesion and mechanical properties are such that the said film may be isolable and manipulable in isolation, for example, when the said film is prepared by pouring onto a non-stick surface, for instance, a Teflon-coated or silicone-coated surface.

It is preferable that the (g) film-forming polymer be present in the form of particles dispersed in an aqueous phase, in particular in the form of a latex.

Among film-forming polymers that may be used in the composition of the present invention, mention may be made of synthetic polymers, of the free-radical type or of the polycondensate type, polymers of natural origin, and mixtures thereof.

The (g) film-forming polymer according to the present invention may be selected from vinyl (co)polymers, (meth) acrylic (co)polymers, urethanes (co)polymers, and mixtures thereof. Advantageously, the film-forming polymer is selected from a styrene-(meth)acrylic and (meth)acrylic copolymer, a vinyl acetate and (meth)acrylic copolymer, and mixtures thereof.

The film-forming polymers of the free-radical type may be chosen, for example, from vinyl polymers or copolymers, such as acrylic polymers.

The vinyl film-forming polymers can result from the polymerization of monomers comprising at least one ethylenic unsaturation and at least one acidic group and/or esters of these acidic monomers and/or amides of these acidic monomers.

Monomers comprising at least one acid group which may be used include, for example, α,β-ethylenic unsaturated carboxylic acids such as acrylic acid, methacrylic acid, crotonic acid, maleic acid or itaconic acid. (Meth)acrylic acid and crotonic acid may, for example, be used. In one embodiment, (meth)acrylic acid is used.

The esters of acidic monomers are chosen, for example, from (meth)acrylic acid esters (also known as (meth)acrylates), such as (meth)acrylates of an alkyl, for example, a $C_1$-$C_{30}$ alkyl, such as a $C_1$-$C_{20}$ alkyl, (meth)acrylates of an aryl, such as a $C_6$-$C_{10}$ aryl, and (meth)acrylates of a hydroxyalkyl, such as a $C_2$-$C_6$ hydroxyalkyl.

Among the alkyl (meth)acrylates that may be mentioned, examples include methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates that may be mentioned, examples include hydroxyethyl acrylate, 2-hydroxypropyl acrylate, hydroxyethyl methacrylate and 2-hydroxypropyl methacrylate.

Among the aryl (meth)acrylates that may be mentioned, examples include benzyl acrylate and phenyl acrylate.

The (meth)acrylic acid esters that may be used are, for example, alkyl (meth)acrylates.

As disclosed herein, the alkyl group of the esters may be either fluorinated or perfluorinated, i.e., some or all of the hydrogen atoms of the alkyl group are substituted with fluorine atoms.

Examples of amides of the acid monomers that may be mentioned include (meth)acrylamides, such as N-alkyl (meth)acrylamides, for example, of a $C_2$-$C_{12}$ alkyl. Among the N-alkyl(meth)acrylamides that may be mentioned, examples include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above.

Examples of vinyl esters that may be mentioned include vinyl acetate, vinyl neodecanoate, vinyl pivalate, vinyl benzoate and vinyl t-butylbenzoate. Styrene monomers that may be mentioned include styrene and α-methylstyrene.

Among the film-forming polycondensates that may be mentioned, examples include polyurethanes, polyesters, polyesteramides, polyamides, epoxyester resins and polyureas.

The polyurethanes may be chosen from anionic, cationic, nonionic or amphoteric polyurethanes, polyurethane-acrylics other than the polyurethane/poly(meth)acrylate graft copolymer, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalene-dicarboxylic acid and 2,6-naphthalenedicarboxylic acid. These dicarboxylic acid monomers may be used alone or as a combination of at least two dicarboxylic acid monomers. Among these monomers, phthalic acid, isophthalic acid and terephthalic acid may, for example, be used.

The diol may be chosen from aliphatic, alicyclic and aromatic diols. The diol used is, for example, chosen from ethylene glycol, diethylene glycol, triethylene glycol, 1,3-propanediol, cyclohexanedimethanol and 4-butanediol. Other polyols that may be used include glycerol, pentaerythritol, sorbitol and trimethylolpropane.

The polyesteramides may be obtained in a manner analogous to that of the polyesters, by polycondensation of diacids with diamines or amino alcohols. Diamines that may be used include, for example, ethylenediamine, hexamethylenediamine and meta- or para-phenylenediamine. An amino alcohol that may be used is, for example, monoethanolamine.

The polyester may also comprise at least one monomer bearing at least one —$SO_3M$ group, wherein M is chosen from a hydrogen atom, an ammonium ion $NH_4^+$ and a metal ion such as an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such an —$SO_3M$ group may, for example, be used.

The aromatic nucleus of the difunctional aromatic monomer also comprising an —$SO_3M$ group as described above may be chosen, for example, from benzene, naphthalene, anthracene, biphenyl, oxybiphenyl, sulfonylbiphenyl and methylenebiphenyl nuclei. Among the difunctional aromatic monomers also comprising an —$SO_3M$ group, mention may be made, for example, of sulfoisophthalic acid, sulfoterephthalic acid, sulfophthalic acid, 4-sulfonaphthalene-2,7-dicarboxylic acid.

The copolymers used are, for example, those based on isophthalate/sulfoisophthalate, such as copolymers obtained by condensation of diethylene glycol, cyclohexanedimethanol, isophthalic acid and sulfoisophthalic acid.

According to one embodiment of the composition according to the present invention, the (g) film-forming polymer may be a liposoluble polymer.

Examples of the liposoluble polymer that may be mentioned include copolymers of a vinyl ester (wherein the vinyl group is directly linked to the oxygen atom of the ester group and the vinyl ester comprises a radical chosen from saturated, linear or branched hydrocarbon-based radicals of 1 to 19 carbon atoms, linked to the carbonyl of the ester group) and of at least one other monomer, which may be a vinyl ester (different from the vinyl ester already present), an α-olefin (comprising from 8 to 28 carbon atoms), an alkyl vinyl ether (the alkyl group of which comprises from 2 to 18 carbon atoms) or an allylic or methallylic ester (comprising a radical chosen from saturated, linear or branched hydrocarbon-based radicals of 1 to 19 carbon atoms, linked to the carbonyl of the ester group).

These copolymers may be crosslinked using crosslinking agents that may be either of the vinylic type or of the allylic or methallylic type, such as tetraallyloxyethane, divinylbenzene, divinyl octanedioate, divinyl dodecanedioate and divinyl octadecanedioate.

Examples of these copolymers which may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Examples of the liposoluble film-forming polymers which may also be mentioned include liposoluble copolymers, such as those resulting from the copolymerization of vinyl esters comprising from 9 to 22 carbon atoms or of alkyl acrylates or methacrylates, wherein the alkyl radicals comprise from 10 to 20 carbon atoms.

Such liposoluble copolymers may be chosen, for example, from polyvinyl stearate, polyvinyl stearate crosslinked with the aid of divinylbenzene, of diallyl ether or of diallyl phthalate copolymers, polystearyl (meth)acrylate, polyvinyl laurate and polylauryl (meth)acrylate copolymers, it being possible for these poly(meth)acrylates to be crosslinked with the aid of ethylene glycol dimethacrylate or tetraethylene glycol dimethacrylate.

The liposoluble copolymers defined above are known and are described, for example, in French patent application FR-A-2 232 303; they may have a weight-average molecular weight ranging, for example, from 2,000 to 500,000 such as from 4,000 to 200,000.

Among the liposoluble film-forming polymers which may be used herein, mention may also be made, for example, of polyalkylenes such as copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) such as copolymers of vinylpyrrolidone and of $C_2$-$C_{40}$ alkene such as $C_3$-$C_{20}$ alkene. Among the VP copolymers which may be used herein, mention may be made, for example, of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

In some embodiments, the film-forming polymer has a Tg (glass transition temperature) value of less than 50° C.

Aqueous dispersions of film-forming polymers which may be used are the acrylic dispersions sold under the names "Neocryl XK-90®", "Neocryl A-1070®", "Neocryl A-1090®", "Neocryl BT-62®", "Neocryl A-1079®" and "Neocryl A-523®" by the company Avecia-Neoresins, "Dow Latex 432®" by the company Dow Chemical, "Daitosol 5000 AD®" or "Daitosol 5000 SJ" by the company Daito Kasey Kogyo; "Syntran 5760" by the company Interpolymer or the aqueous dispersions of polyurethane sold under the names "Neorez R-981®" and "Neorez R-974®" by the company Avecia-Neoresins, "Avalure UR-405®", "Avalure UR-410®", "Avalure UR-425®", "Avalure UR-450®", "Sancure 875®", "Sancure 861®", "Sancure 878®" and "Sancure 2060®" by the company Goodrich, "Impranil 85®" by the company Bayer and "Aquamere H-1511®" by the company Hydromer; vinyl dispersions, for instance "Mexomer PAM" and also acrylic dispersions in isododecane, for instance "Mexomer PAP" by the company Chimex.

The amount of the (g) film-forming polymer(s) in the composition according to the present invention may be 0.01% by weight or more, preferably 0.1% by weight or more, and more preferably 1% by weight or more, relative to the total weight of the composition. It may be even more preferable that the amount of the (g) film-forming polymer(s) in the composition according to the present invention be 5% by weight or more, relative to the total weight of the composition.

On the other hand, the amount of the (g) film-forming polymer(s) in the composition according to the present invention may be 40% by weight or less, preferably 35% by weight or less, and more preferably 30% by weight or less, relative to the total weight of the composition. It may be even more preferable that the amount of the (g) film-forming polymer(s) in the composition according to the present invention be 25% by weight or less, relative to the total weight of the composition.

Accordingly, the amount of the (g) film-forming polymer(s) in the composition may range from 0.01% to 40% by weight, preferably from 0.1% to 35% by weight, and more preferably from 1% to 30% by weight, relative to the total weight of the composition. It may be even more preferable that the amount of the (g) film-forming polymer(s) in the composition according to the present invention be from 5% to 25% by weight, relative to the total weight of the composition.

(Surfactant)

The composition according to the present invention may comprise at least one surfactant. If two or more surfactants are used, they may be the same or different.

Any surfactant may be used for the present invention. The surfactant to be used in the present invention may be selected from the group consisting of anionic surfactants and nonionic surfactants. The surfactant may preferably be selected from nonionic surfactants.

(Anionic Surfactants)

According to the present invention, the type of anionic surfactant is not limited. It may be preferable that the anionic surfactant be selected from the group consisting of ($C_6$-$C_{30}$) alkyl sulfates, ($C_6$-$C_{30}$)alkyl ether sulfates, ($C_6$-$C_{30}$)alkylamido ether sulfates, alkylaryl polyether sulfates, and monoglyceride sulfates; ($C_6$-$C_{30}$)alkylsulfonates, ($C_6$-$C_{30}$) alkylamide sulfonates, ($C_6$-$C_{30}$)alkylaryl sulfonates, α-olefin sulfonates, and paraffin sulfonates; ($C_6$-$C_{30}$)alkyl phosphates; ($C_6$-$C_{30}$)alkyl sulfosuccinates, ($C_6$-$C_{30}$)alkyl ether sulfosuccinates, and ($C_6$-$C_{30}$)alkylamide sulfosuccinates; ($C_6$-$C_{30}$)alkyl sulfoacetates; ($C_6$-$C_{24}$)acyl sarcosinates; ($C_6$-$C_{24}$)acyl glutamates; ($C_6$-$C_{30}$)alkylpolyglycoside carboxylic ethers; ($C_6$-$C_{30}$)alkylpolyglycoside sulfosuccinates; ($C_6$-$C_{30}$)alkyl sulfosuccinamates; ($C_6$-$C_{24}$)acyl isethionates; N—($C_6$-$C_{24}$)acyl taurates; $C_6$-$C_{30}$ fatty acid salts; coconut oil acid salts or hydrogenated coconut oil acid salts; ($C_8$-$C_{20}$)acyl lactylates; ($C_6$-$C_{30}$)alkyl-D-galactoside uronic acid salts; polyoxyalkylenated ($C_6$-$C_{30}$)alkyl ether carboxylic acid salts; polyoxyalkylenated ($C_6$-$C_{30}$)alkylaryl ether carboxylic acid salts; and polyoxyalkylenated ($C_6$-$C_{30}$)alkylamido ether carboxylic acid salts.

It may be more preferable that the anionic surfactant be selected from salts of ($C_6$-$C_{30}$)alkyl sulfate or polyoxyalkylenated ($C_6$-$C_{30}$)alkyl ether carboxylic acid salts.

In at least one embodiment, the anionic surfactants are in the form of salts such as salts of alkali metals, for instance sodium; salts of alkaline-earth metals, for instance magnesium; ammonium salts; amine salts; and amino alcohol salts. Depending on the conditions, they may also be in acid form.

(Nonionic Surfactants)

The nonionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; fatty acid esters of sorbitan; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)

alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; and mixtures thereof.

The nonionic surfactants may preferably be chosen from monooxyalkylenated, polyoxyalkylenated, monoglycerolated or polyglycerolated nonionic surfactants. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:
monooxyalkylenated or polyoxyalkylenated ($C_8$-$C_{24}$)alkylphenols,
saturated or unsaturated, linear or branched, monooxyalkylenated or polyoxyalkylenated $C_8$-$C_{30}$ alcohols,
saturated or unsaturated, linear or branched, monooxyalkylenated or polyoxyalkylenated $C_8$-$C_{30}$ amides,
esters of saturated or unsaturated, linear or branched, $C_8$-$C_{30}$ acids and of polyalkylene glycols, monooxyalkylenated or polyoxyalkylenated esters of saturated or unsaturated, linear or branched, $C_8$-$C_{30}$ acids and of sorbitol,
saturated or unsaturated, monooxyalkylenated or polyoxyalkylenated plant oils,
condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50. Advantageously, the nonionic surfactants do not comprise any oxypropylene units.

According to one of the embodiments of the present invention, the polyoxyalkylenated nonionic surfactants are chosen from polyoxyethylenated fatty alcohol (polyethylene glycol ether of fatty alcohol), polyoxyethylenated fatty ester (polyethylene glycol ester of fatty acid), and mixture of polyoxyethylenated fatty alcohol and polyoxyethylenated fatty ester.

Examples of polyoxyethylenated fatty alcohol (or $C_8$-$C_{30}$ alcohols) that may be mentioned include the adducts of ethylene oxide with lauryl alcohol, especially those containing from 2 to 50 oxyethylene units and more particularly those containing from 2 to 20 oxyethylene units (Laureth-2 to Laureth-20, as the CTFA names); the adducts of ethylene oxide with behenyl alcohol, especially those containing from 2 to 50 oxyethylene units and more particularly those containing from 2 to 20 oxyethylene units (Beheneth-2 to Beheneth-20, as the CTFA names); the adducts of ethylene oxide with cetearyl alcohol (mixture of cetyl alcohol and stearyl alcohol), especially those containing from 2 to 30 oxyethylene units (Ceteareth-2 to Ceteareth-30, as the CTFA names); the adducts of ethylene oxide with cetyl alcohol, especially those containing from 2 to 30 oxyethylene units (Ceteth-2 to Ceteth-30, as the CTFA names); the adducts of ethylene oxide with stearyl alcohol, especially those containing from 2 to 50 oxyethylene units and more particularly those containing from 2 to 20 oxyethylene units (Steareth-2 to Steareth-20, as the CTFA names); the adducts of ethylene oxide with isostearyl alcohol, especially those containing from 2 to 50 oxyethylene units (Isosteareth-2 to Isosteareth-50, as the CTFA names); and mixtures thereof.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

According to one preferred embodiment of the invention, the composition according to the present invention comprises at least one polyoxyethylenated fatty alcohol.

According to a more preferred embodiment, the composition according to the invention contains at least one fatty alcohol comprising from 2 to 9 ethyleneoxide units and at least one fatty alcohol comprising from 10 to 30 ethyleneoxide units.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

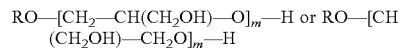

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The monoglycerolated or polyglycerolated $C_8$-$C_{40}$ fatty esters may correspond to the following formula:

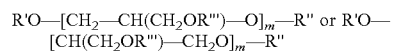

in which each of R', R" and R'" independently represents a hydrogen atom, or a linear or branched $C_8$-$C_{40}$ and preferably $C_8$-$C_{30}$ alkyl-CO— or alkenyl-CO-radical, with the proviso that at least one of R', R" and R'" is not a hydrogen atom, and m represents a number ranging from 1 to 30 and preferably from 1.5 to 10.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

Preferably, the composition according to the present invention comprises a nonionic surfactant with an HLB of greater than or equal to 8, preferably from 8 to 18. The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984). More preferably, the composition according to the present invention comprises a nonionic surfactant with an HLB of greater than or equal to 8 as well as a nonionic surfactant with an HLB of lower than 8.

According to one embodiment of the present invention, the amount of the surfactant(s) may range from 0.1 to 20% by weight, preferably from 0.5 to 10% by weight, and more preferably from 1 to 5% by weight, relative to the total weight of the composition according to the present invention.

(Fiber)

The composition according to the present invention may comprise at least one fiber. If two or more fibers are used, they may be the same or different.

In some embodiments, the composition according to the present invention may further comprise at least one fiber to allow an improvement in the lengthening effect for keratin fibers. The fibers useful in the present invention may be chosen from rigid or non-rigid fibers and may be of natural or synthetic fibers. Natural fibers include, but are not limited to, cotton, silk, wool, and other keratin fibers. Synthetic fibers include, but are not limited to, polyester, rayon, nylon, and other polyamide fibers. In some embodiments, fibers may be made of non-rigid fibers such as polyamide (Nylon®) fibers, or rigid fibers such as polyimide-amide fibers, for instance, those sold under the trade name "Kermel" and "Kermel Tech" by Rhodia, or poly(p-phenyleneterephthalamide) (or aramid) fibers sold especially under the name Kevlar® by DuPont de Nemours.

The fiber may be present in the composition according to the present invention in an amount generally ranging from 0.01% to 10% by weight, and preferably from 0.1% to 5% by weight, of the total weight of the composition, including all ranges and subranges therebetween.

[Filler]

The composition according to the present invention may comprise at least one filler. If two or more fillers are used, they may be the same or different.

In some embodiments, the composition according to the present invention may further comprise a filler selected from those that are well known to a person skilled in the art and commonly used in cosmetic compositions. Filler should be understood to mean lamellar or non-lamellar, inorganic or organic particles. Representative examples of these ingredients include mica, silica, kaolin, iron oxides, titanium dioxide, polyamide powders, polyamide powders, for instance Nylon® (Orgasol from Atochem), poly-alanine powders, polyethylene powders, tetrafluoroethylene polymer powders, for instance Teflon®, lauroyllysine, starch, boron nitride, hollow polymer microspheres such as those of polyvinylidene chloride/acrylonitrile, for instance Expancel® (Nobel Industrie), acrylic powders such as Polytrap® (Dow Corning), polymethyl methacrylate particles and silicone resin microbeads (for example, Tospearls® from Toshiba), precipitated calcium carbonate, magnesium carbonate, magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms, preferably from 12 to 18 carbon atoms, for example, zinc stearate, magnesium stearate, lithium stearate, zinc laurate, or magnesium myristate.

As the filler, the composition according to the present invention preferably comprises a silicone elastomer. The silicone elastomer used in the present invention may be chosen from non-emulsifying elastomers, such as Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name).

The silicone elastomers are described especially in patents EP 242 219, EP 285 886 and EP 765 656 and in patent application JP-A-61-194009.

The silicone elastomer is generally in the form of a gel, a paste or a powder, but advantageously in the form of a gel in which the silicone elastomer is dispersed in a linear silicone oil (dimethicone) or cyclic silicone oil (e.g.: cyclopentasiloxane), advantageously in a linear silicone oil.

The elastomers that may be used more particularly include those sold under the names KSG-6, KSG-15, KSG-16, KSG-18, KSG-41, KSG-42, KSG-43 and KSG-44 by the company Shin-Etsu, DC9040, DC9041 and DC9042 by the company Dow Corning, and SFE 839 by the company General Electric.

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, optionally modified with optionally fluorinated aliphatic groups, or with functional groups such as hydroxyl, thiol and/or amine groups.

Mention may be made especially of the compounds having the following INCI names:

dimethicone/vinyl dimethicone crosspolymer, such as USG-105 and USG-107A from the company Shin-Etsu; DC9506 and DC9701 from the company Dow Corning;

dimethicone/vinyl dimethicone crosspolymer (and) dimethicone, such as KSG-6 and KSG-16 from the company Shin-Etsu;

dimethicone/vinyl dimethicone crosspolymer (and) cyclopentasiloxane, such as KSG-15;

cyclopentasiloxane (and) dimethicone crosspolymer, such as DC9040, DC9045 and DC5930 from the company Dow Corning;

dimethicone (and) dimethicone crosspolymer, such as DC9041 from the company Dow Corning;

dimethicone (and) dimethicone crosspolymer, such as Dow Corning EL-9240® Silicone Elastomer Blend from the company Dow Corning (mixture of polydimethylsiloxane crosslinked with hexadiene/polydimethylsiloxane (2 cSt));

C4-24 alkyl dimethicone/divinyl dimethicone crosspolymer, such as NuLastic Silk MA from the company Alzo.

The composition according to the present invention preferably comprises a silicone elastomer selected from those having the INCI name of Dimethicone/Vinyl Dimethicone Crosspolymer.

The filler may be present in the composition according to the present invention in an amount generally ranging from 0.1% to 25% by weight, and preferably from 1% to 20% by weight, of the total weight of the composition, including all ranges and subranges therebetween.

[Dyestuff]

The composition according to the present invention may comprise at least one dyestuff. If two or more dyestuffs are used, they may be the same or different.

Suitable dyestuffs include but are not limited to pulverulent dyestuff, liposoluble dyes, and water-soluble dyes.

The pulverulent dyestuffs may be chosen from pigments and nacres.

The pigments, which may be used according to the present invention, may be chosen from white, colored, inorganic, organic, polymeric, nonpolymeric, coated and uncoated pigments. Representative examples of inorganic pigments include metallic oxide, such as titanium dioxide, optionally surface-treated, zirconium oxide, zinc oxide, cerium oxide, iron oxide, chromium oxide, manganese violet, ultramarine blue, chromium hydrate, and ferric blue. Representative examples of organic pigments include carbon black, pigments of D&C type, and lakes based on cochineal carmine, barium, strontium, calcium, and aluminum. As the pigments, the composition according to the present invention preferably comprises at least one metallic oxide, in particular iron oxide.

The nacres which may be used according to the present invention may be chosen from white nacreous pigments such as mica coated with titanium or with bismuth oxychloride, colored nacreous pigments such as titanium mica with iron oxides, titanium mica with iron oxides, titanium mica with ferric blue or chromium oxide, titanium mica with an organic pigment chosen from those mentioned above, and nacreous pigments based on bismuth oxychloride.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

The water-soluble dyes which may be used according to the present invention include beetroot juice, methylene blue, the disodium salt of ponceau, the disodium salt of alizarin green, quinoline yellow, the trisodium salt of amaranth, the disodium salt of tartrazine, the monosodium salt of rhodamine, the disodium salt of fuchsin, and xanthophyll.

The dyestuff may be present in the composition according to the present invention in an amount generally ranging from 0.01% to 20% by weight, and preferably from 0.1% to 10% by weight, of the total weight of the composition, including all ranges and subranges therebetween.

The pigments may be present in the composition according to the present invention in an amount of generally 2% by weight or more, preferably from 3 to 15% by weight, relative to the total weight of the composition.

(Other Optional Additives)

The composition according to the present invention may also comprise any other optional additive(s) usually used in the field of cosmetics, chosen, for example, from polymers other than film-forming polymers, solvents, gums, resins, hydrophilic thickening agents such as hydroxypropylcellulose and hydroxyethylcellulose, hydrophobic thickening agents such as dimethicone crosspolymers, dispersants, antioxidants, preserving agents such as phenoxyethanol, fragrances, neutralizers, pH adjusting agents such as triethanolamine, antiseptics, UV-screening agents, cosmetic active agents, such as vitamins, moisturizers, emollients or collagen-protecting agents, and mixtures thereof.

The composition according to the present invention may include one or several cosmetically acceptable organic solvents, which may be alcohols: in particular monovalent alcohols such as ethyl alcohol, isopropyl alcohol, benzyl alcohol, and phenylethyl alcohol; diols such as ethylene glycol, propylene glycol, and butylene glycol; other polyols such as glycerol, sugar, and sugar alcohols; and ethers such as ethylene glycol monomethyl, monoethyl, and monobutyl ethers, propylene glycol monomethyl, monoethyl, and monobutyl ether, and butylene glycol monomethyl, monoethyl, and monobutyl ethers.

The organic solvent(s) may then be present in a concentration of from 0.01% to 30% by weight, preferably from 0.1% to 20% by weight, and more preferably from 1% to 15% by weight, relative to the total weight of the composition.

It is a matter of routine operations for a person skilled in the art to adjust the nature and amount of the above optional additives which may be present in the composition in accordance with the present invention such that the desired cosmetic properties are not thereby affected.

[Preparation]

The composition according to the present invention can be prepared by mixing the above-described essential and optional ingredients in a conventional manner.

For example, the composition according to the present invention can be prepared by a process comprising the step of mixing (a) at least one botanical butter;
(b) at least one alkaline agent comprising at least one primary amino group and at least three hydroxyl groups;
(c) at least one wax; and
(d) water.

It is possible to further mix any of the optional ingredients.

It may be preferable that the (a) botanical butter(s) and the (c) wax be mixed firstly to prepare a fatty mixture, and then the fatty mixture thus prepared be further mixed with the (b) alkaline agent(s) and (d) water to obtain the composition according to the present invention. It may be more preferable that the (b) alkaline agent(s) and (d) water be mixed to obtain a hydrophilic mixture, and then the hydrophilic mixture be further mixed with the fatty mixture.

The mixing can be performed at any temperature, preferably at a temperature of 55° C. or more, preferably 65° C. or more, and more preferably 75° C. or more. It is preferable to further mix with any of the above-described optional ingredients.

It is preferable that the composition according to the present invention be in the form of a liquid, preferably a dispersion of fatty phases including (a) botanical butter(s) and (c) wax(es) dispersed in a continuous aqueous phase including (b) alkaline agent(s) and (d) water.

[Cosmetic Use and Process]

The composition according to the present invention may be a cosmetic composition, preferably a makeup cosmetic composition (in particular, an eye makeup cosmetic composition), and more preferably a mascara.

The cosmetic composition according to the present invention can be used for cosmetic treatments, preferably makeup, of keratin fibers such as hair, eyebrow and eyelash.

For example, the composition according to the present invention can be used for a cosmetic process for making up keratin fibers in particular eyelash comprising the step of applying onto the keratin fibers the composition according to the present invention.

The composition according to the present invention can provide keratin fibers with cosmetic effects, in particular makeup effects, with even application of the composition. Furthermore, the composition according to the present invention may exert lengthening effects for keratin fibers such as eyelash and long-lasting makeup effects.

It is preferable that the composition according to the present invention does not comprise any substantial amount of triethanolamine, although it may comprise a minor or insubstantial amount of triethanoamine. The amount of triethanolamine in the composition according to the present invention may be 0.1% by weight or less, preferably 0.05% by weight or less, and more preferably 0.01% by weight or less, relative to the total weight of the composition.

EXAMPLES

The present invention will be described in a more detailed manner by way of examples. However, these examples should not be construed as limiting the scope of the present invention. The examples below are presented as non-limiting illustrations in the field of the invention.

Examples 1 to 2 and Comparative Examples 1 to 4

[Preparations]

The following compositions according to Examples (Ex.) 1 to 2 and Comparative Examples (Comp. Ex.) 1 to 4, shown in Table 1, were prepared as a mascara in the form of an O/W emulsion by mixing the components shown in Table 1 at 80° C. The numerical values for the amounts of the components shown in Table 1 are all based on "% by weight" as active raw materials unless otherwise indicated.

TABLE 1

|  | Ex. 1 | Ex. 2 | Comp. Ex. 1 | Comp. Ex. 2 | Comp. Ex. 3 | Comp. Ex. 4 |
| --- | --- | --- | --- | --- | --- | --- |
| Stearic Acid | 2.50 | 2.50 | 2.50 | 2.50 | 2.50 | 2.50 |
| Steareth-20 | 1.50 | 1.50 | 1.50 | 1.50 | 1.50 | 1.50 |
| Sorbitan Stearate | 1.50 | 1.50 | 1.50 | 1.50 | 1.50 | 1.50 |
| Sucrose Tristearate | 1.00 | 1.00 | 1.00 | 1.00 | 1.00 | 1.00 |
| Jojoba Butter (ISO JOJOBA 50 by DESERT WHALE) | 2.00 | 2.80 | — | 2.00 | 2.00 | 2.00 |
| Carnauba Wax | 7.00 | 9.80 | 9.00 | 7.00 | 7.00 | 7.00 |
| Bees Wax | 9.00 | 12.60 | 9.00 | 7.00 | 7.00 | 7.00 |
| Water | 50.97 | 43.77 | 50.97 | 50.72 | 51.08 | 51.23 |
| Sodium Dehydroacetate | 0.30 | 0.30 | 0.30 | 0.30 | 0.30 | 0.30 |
| Disodium EDTA | 0.05 | 0.05 | 0.05 | 0.05 | 0.05 | 0.05 |
| Tromethamine | 1.08 | 1.08 | 1.08 | — | — | — |
| Triethanolamine | — | — | — | 1.33 | — | — |
| Aminomethylpropanediol | — | — | — | — | 0.97 | — |
| Aminomethylpropanol | — | — | — | — | — | 0.82 |
| Phenoxyethanol | 0.70 | 0.70 | 0.70 | 0.70 | 0.70 | 0.70 |
| Pentylene Glycol | 0.50 | 0.50 | 0.50 | 0.50 | 0.50 | 0.50 |
| Caprylyl Glycol | 0.50 | 0.50 | 0.50 | 0.50 | 0.50 | 0.50 |
| Acasia Senegal Gum | 0.50 | 0.50 | 0.50 | 0.50 | 0.50 | 0.50 |
| Polyvinyl Alcohol | 1.00 | 1.00 | 1.00 | 1.00 | 1.00 | 1.00 |
| Hydroxyethyl Cellulose | 0.40 | 0.40 | 0.40 | 0.40 | 0.40 | 0.40 |
| Iron Oxides | 5.00 | 5.00 | 5.00 | 5.00 | 5.00 | 5.00 |
| Silica | 0.50 | 0.50 | 0.50 | 0.50 | 0.50 | 0.50 |
| Dimethicone (and) Dimethicone/Vinyl Dimethicone Crosspolymer (KSG 16, by Shin-Etsu) | 1.50 | 1.50 | 1.50 | 1.50 | 1.50 | 1.50 |
| Nylon-6 (and) Iron Oxides (and) Silica (and) Triethoxycaprylylsilane | 0.50 | 0.50 | 0.50 | 0.50 | 0.50 | 0.50 |
| Acrylates Copolymer (DAITOSOL 5000 AD by DAITO KASEI KOGYO) | 5.00 | 5.00 | 5.00 | 5.00 | 5.00 | 5.00 |
| Styrene/Acrylates/Ammonium Methacrylate Copolymer (SYNTRAN 5760 CG by INTERPOLYMER) | 5.00 | 5.00 | 5.00 | 5.00 | 5.00 | 5.00 |
| Ethanol | 2.00 | 2.00 | 2.00 | 2.00 | 2.00 | 2.00 |
| Total | 100.00 | 100.00 | 100.00 | 100.00 | 100.00 | 100.00 |
| Volume | Good | Good | Fair | Fair | Poor | Poor |
| Cleanness | Good | Fair | Fair | Poor | Poor | Poor |

[Evaluations]

(Volume)

Each of the compositions according to Examples 1 and 2, and Comparative Examples 1-4 was applied onto the eyelash of panelists, and the volume of the applied eyelash was evaluated by visual observation in accordance with the score of from 1 to 10. The average of the score was categorized in accordance with the following criteria.

Good: 7.0 or more
Fair: From 4.0 to 7.0
Poor: 4.0 or less

The results are shown in Table 1.

(Cleanness)

Each of the compositions according to Examples 1 and 2, and Comparative Examples 1-4 was applied onto the eyelash of panelists, and the cleanness (even application or no irregularities in thickness of applied eyelash) of the applied eyelash was evaluated by visual observation in accordance with the score of from 1 to 10. The average of the score was categorized in accordance with the following criteria.

Good: 7.0 or more
Fair: From 4.0 to 7.0
Poor: 4.0 or less

The results are shown in Table 1.

(Summary)

The composition according to Example 1, which includes jojoba butter and tromethamine shows the best results in terms of volume and cleanness.

The composition according to Example 2, which includes more amount of jojoba butter than Example 2, shows good results in terms of volume.

The composition according to Comparative Example 1, which includes carnauba wax instead of jojoba butter in the composition according to Example 1, did not show good results in terms of volume and cleanness.

The composition according to Comparative Example 2, which includes triethanolamine instead of tromethamine in the composition according to Example 1, did not show good results in terms of volume and cleanness.

The composition according to Comparative Example 3, which includes aminomethylpropanediol instead of tromethamine in the composition according to Example 1, did not show good results in terms of volume and cleanness.

The composition according to Comparative Example 4, which includes aminomethylpropanol instead of tromethamine in the composition according to Example 1, did not show good results in terms of volume and cleanness.

The invention claimed is:

1. A cosmetic process for making up eyelashes comprising the step of applying onto the eyelashes a mascara composition comprising:
   (a) jojoba butter in an amount ranging from 1.5% by weight or more, relative to the total weight of the mascara composition;
   (b) tromethamine in an amount ranging from 0.5% to 10% by weight, relative to the total weight of the mascara composition;
   (c) at least one wax with a melting point of greater than or equal to 60° C. in an amount ranging from 10% by weight or more, relative to the total weight of the mascara composition; and
   (d) water.

2. The process according to claim 1, wherein the jojoba butter has a melting point of less than 60° C.

3. The process according to claim 1, wherein the amount of the jojoba butter in the composition is 1.5% to 20% by weight, relative to the total weight of the composition.

4. The process according to claim 1, wherein the at least one wax is chosen from carnauba wax, beeswax or mixtures thereof.

5. The process according to claim 1, wherein the amount of the at least one wax in the composition is 10% to 40% by weight, relative to the total weight of the composition.

6. The process according to claim 1, wherein the amount of the water in the composition is 25% to 75% by weight, relative to the total weight of the composition.

7. The process according to claim 1, wherein the composition further comprises (e) at least one fatty acid.

8. The process according to claim 7, wherein the amount of the at least one fatty acid in the composition is 0.01% to 20% by weight, relative to the total weight of the composition.

9. The process according to claim 7, wherein the at least one alkaline agent forms at least one soap with the at least one fatty acid.

10. The process according to claim 1, wherein the composition further comprises particles chosen from at least one filler or at least one pigment.

11. The process according to claim 10, wherein the at least one pigment is chosen from metallic oxides, and the at least one filler is chosen from silicone elastomers.

12. The process according to claim 10, wherein the amount of the particles in the composition is 2% by weight or more, relative to the total weight of the composition.

13. The process according to claim 1, wherein the composition further comprises at least one non-ionic surfactant selected from non-ionic surfactant(s) having HLB value of greater than or equal to 8.

* * * * *